US006048732A

United States Patent [19]
Anslyn et al.

[11] Patent Number: 6,048,732
[45] Date of Patent: Apr. 11, 2000

[54] RECEPTOR AND METHOD FOR CITRATE DETERMINATION

[75] Inventors: Eric V. Anslyn, Austin, Tex.; Axel Metzger, Plainsboro, N.J.

[73] Assignee: Board of Regents, The University of Texas System, Austin, Tex.

[21] Appl. No.: 08/950,712

[22] Filed: Oct. 15, 1997

Related U.S. Application Data

[60] Provisional application No. 60/028,630, Oct. 16, 1996.

[51] Int. Cl.⁷ ................................................. G01N 31/22
[52] U.S. Cl. ........................................... 436/129; 436/166
[58] Field of Search ................................... 436/127, 128, 436/129, 166

[56] References Cited

U.S. PATENT DOCUMENTS

| | | | |
|---|---|---|---|
| 3,490,874 | 1/1970 | Ando et al. ................................. | 23/230 |
| 4,894,346 | 1/1990 | Myers et al. ............................... | 436/85 |

FOREIGN PATENT DOCUMENTS

| | | | |
|---|---|---|---|
| 192194 | 4/1967 | U.S.S.R. ................................. | 436/129 |

OTHER PUBLICATIONS

E. Szekely, "Complexometric Determination of Citric Acid with Copper." Talanta, 153–154, Feb. 1985.

Lin, T.I., Lee, Y. H., and Chen, Y. C. "Capillary Electrophoretic Analysis of Inorganic Cations Role of Complexing Agent and Buffer pH." Journal of Chromatography A, 167–176, Nov. 1993.

Metzger, A. and Anslyn E. V. "A Chemosensor for Citrate in Beverages." Angew. Chem. Int. Ed., 649–651, Mar. 1998.

Wilcox, Craig S. et al., "New Approaches to Synthetic Receptors, Synthesis and Host Properties of a Water Soluble Macrocyclic Analog of Tröger's Base," Tetrahedron Letters, vol. 27, No. 40, 1986, Pergamon Journals Ltd., pp. 5563–5566.

Stack, T.D.P. et al., "Rational Reduction of the Conformational Space of a Siderophore Analog Through Nonbonded Interactions: The Role of Entropy in Enterobactin," J. Am. Chem. Soc., 1993, 115, pp. 6466–6467.

Weitl, Frederick L. et al., "Ferric Ion Sequestering Agents. 1. Hexadentate O–Bonding N,N',N"—Tris(2,3–dihydroxybensoyl) Derivatives of 1,5,9—Triazacyclotridecane and 1,3,5—Triaminomethylbenzene," Journal of the American Chemical Society, vol. 101, No. 10, May 9, 1979, pp. 2728–2731.

Adams, Stephen R., "Fluorescence Ratio Imaging of Cyclic AMP in Single Cells," Nature, vol. 349, Feb. 21, 1991, pp. 694–697.

Albert, Jeffrey S., "Molecular Recognition of Proteins: Sequence–Selective Binding of Aspartate Pairs in Helical Peptides," J. Am. Chem. Soc., 1995, vol. 117, No. 1143–1144.

Bell, T.W., "Detection of Creatinine by a Designed Receptor," Science, vol. 269, Aug. 4, 1995, pp. 671–674.

Benesi, H.A. et al., "A Spectrophotometric Investigation of the Interaction of Iodine with Aromatic Hydrocarbons," J. Am. Chem. Soc., vol. 71, pp. 2703–2707.

Berger, M. et al., "Electroneutral Artificial Hosts for Oxoanions Active in Strong Donor Solvents," J. Am. Chem. Soc., 1996, vol. 118, pp. 8947–8948.

Perry, M.J., *Monoclonal Antibodies: Principles and Applications*, 1995 Wiley–Liss, Inc., pp. 107–120.

Bramhall, J. et al., "Temperature Dependence of Membrane Ion Conductance Analyzed by Using the Amphiphilic Anion 54/6–Carboxyfluorescein," Biochemistry, 1987, vol. 26, pp. 6330–6340.

Cram, D. et al., "Concept, Structure, and Binding in Complexation," Top. Curr. Chem., 1998, pp. 45–50.

Cram, D., "The Design of Molecular Hosts, Guests, and Their Complexes (Novel Lecture)**," Angewandte Chemie International Edition in English, vol. 27. No. 8, Aug. 1988, pp. 1009–1112.

De Mendoza et al., "Molecular Recognition of Organic Acids and Anions," Top. Curr. Chem., vol. 175, 1995, pp. 103–110.

Diederich, F., "Complexation of Arenes by Macrocyclic Hosts in Aqueous and Organic Solutions," J. Am. Chem. Soc., 1986, vol. 108, pp. 2273–2286.

Dietrich, B., "Anion Coordination Chemistry: Polyguanidinium Salts as Anion Complexones," Helvetica Chimica Acta, vol. 62, Fasc. 8, 1979, Nr. 280, pp. 2763–2787.

Fabbrizzi, L., "Sensors and Switches from Supramolecular Chemistry," Chem. Soc. Rev., 1995, pp. 197–202.

Diamond et al., "Calixarene–based Sensing Agents," Chem. Soc. Rev., 1996, pp. 15–24.

Fan, E. et al., "Molecular Recognition: Hydrogen–Bonding Receptors That Function in Highly Competitive Solvents," J. Am. Chem. Soc., 1993, vol. 115, pp. 369–370.

Godwin, H. et al., "A Fluorescent Zinc Probe Based on Metal–Induced Peptide Folding," J. Am. Chem. Soc., 1996, vol. 118, pp. 6514–6515.

Graber, M., "Characteristics of Fluoroprobes for Measuring Intracellular pH," Analytical Biochemistry, 1986, vol. 156, pp. 202–212.

James, T., "A Glucose–Selective Molecular Fluorescence Sensor," Angew. Chem. Int. Ed. Engl., 1994, vol. 33, No. 21, pp. 2207–2208.

(List continued on next page.)

*Primary Examiner*—Jill Warden
*Attorney, Agent, or Firm*—Conley, Rose & Tayon, PC

[57] ABSTRACT

A sensing composition for polycarboxylic acids which operates in competitive solvents. The composition includes a receptor and an indicator, both of which are mixed in a solvent. Addition of a polycarboxylic acid to the composition causes a change in the physical properties of the composition. Measurement of the amount of change in solution allows the concentration of polycarboxylic acid to be determined. The sensor is preferably selective for polycarboxylic acids, is sensitive, and may be used to analyze solutions of polycarboxylic acids.

22 Claims, 9 Drawing Sheets

OTHER PUBLICATIONS

Kilway, K. et al., "Effect of Transition–Metal Complexation on the Stereodynamics of Persubstituted Arenes. Evidence for Steric Complementarity Between Arene and Metal Tripod," J. Am. Chem. Soc., 1992, vol. 114, pp. 255–261.

Kneeland, D. et al., "Bis (alkylguanidinium) Receptors for Phosphodiesters: Effect of Counterions, Solvent Mixtures, and Cavity Flexibility on Complexation," J. Am. Chem. Soc., 1993, vol. 115, pp. 10042–10055.

Lehn, J.M., "Cryptates: Inclusion Complexes of Macropolycyclic Receptor Molecules," Pure & Appl. Chem. 1978, vol. 50, pp. 871–892.

Lehn, J.M., "Macrocyclic Receptor Molecules: Aspects of Chemical Reactivity, Investigations Into Molecular Catalysis and Transport Processes," Pure & Appl. Chem. 1979, vol. 51, pp. 979–997.

Metzger, A., "A Convenient Access to Chiral Monofunctionalized Bicyclic Guanidinium Receptor Groups," Synthesis, 1995, pp. 566–570.

Mortellaro, M. et al., "A Turn–On For optical Sensing," Chemtech, Feb. 1996, vol. 26, pp. 17–23.

Perreault, D. et al., "The Advantages of Using Rigid Polyaza–Clefts for Hydrogen–Bonding Molecular Recognition," Tetrahedron, 1995, vol. 51, No. 2, pp. 353–362.

Peterson, B. et al., "Steroid Complexation by Cyclophane Receptors in Aqueous Solution: Substrate Selectivity, Enthalpic Driving Force for Cavity Inclusion, and Enthalpy–Entropy Compensation," Tetrahedron, 1995, vol. 51, No. 2, pp. 401–421.

Pikramenou, Z. et al., "Synthesis of a Cradle Cyclodextrin," Tetrahedron Letters, 1993, vol. 34, pp. 3531–3534.

Schießl, P. et al., "Abiotic Molecular Recognition of Dicarboxylic Anions in Methanol," Tetrahedron Letters, 1993, vol. 34, No. 15, pp. 2449–2452.

Schneider, H., "Mechanisms of Molecular Recognition: Investigations of Organic Host–Guest Complexes," Angew. Chem. Int. Ed. Engl., 1991, vol. 30, pp. 1417–1436.

Metzger, A. et al., "A Synthetic Receptor Selective for Citrate," Angew. Chem. Int. Ed. Eng., 1997, vol. 36, pp. 862–865.

Connors, K., *Binding Constants—The Measurement of Molecular Complex Stability*, John Wiley & Sons, 1987, pp. 189–215.

Czarnik, A.W., "Desparately Seeking Sensors", Chemistry & Biology, 1995, vol. 2, pp. 423–428.

Hannon, C.L. et al., "The Guanidinium Group: Its Biological Role and Synthetic Anologs", Bioorganic Chemistry Frontiers, Springer–Verlag, Berlin, vol. 3, pp. 193–255.

Receptor 1

Receptor 2

Receptor 3

RECEPTOR AND METHOD FOR CITRATE DETERMINATION

PRIORITY CLAIM

This application claims the benefit of U.S. Provisional Application Ser. No. 60/028,630 entitled "Selective Receptor For Citrate And Use For Citrate Determination," filed Oct. 16, 1996.

BACKGROUND OF THE INVENTION

1. Field of the Invention

The present invention generally relates to a method for determining the concentration of polycarboxylic acids in a solution. More particularly, an embodiment of the invention relates to a receptor for polycarboxylic acids and a method for using the receptor for determining the concentration of a polycarboxylic acid in a solution.

2. Description of the Related Art

Selective binding of ions in highly competitive media, such as water, has intrigued chemists for many years (Cram and Trueblood, *Top. Curr. Chem.*, 98:43, 1981). The binding of biologically active anions, e.g., phosphates or carboxylates, has been one focus of interest for investigations which aim to mimic enzymes or transport proteins (Kneeland et al., *J. Am. Chem. Soc.*, 115:10042, 1993; De Mendoza et al., *Top. Curr. Cyhem.*, 175:101, 1995). These investigations are typically focused upon binding strength and selectivity. The first may be regulated by the choice of functional groups or solvent systems. The second may be achieved by introducing elements complementary to the shape and binding characteristics of the substrate (Lehn, *Supramolecular Chemistry, Concepts and Perspective*, VCH, New York, 1995; Cram, *Angew. Chem. Int. Ed. Engl.*, 27:1009, 1988).

The field of molecular recognition is becoming sophisticated enough that both binding strength and selectivity may be tuned for many classes of guests (Schneider, *Angew. Chem. Int. Ed. Engl.*, 30:1417, 1991). Strong and selective binding of hydrophilic guests, however, in high dielectric media is still elusive.

Citrate, a tricarboxylic acid at near neutral pH, is hydrophilic and highly charged. Citrate is also of commercial interest because of its abundance in citrus fruits and common beverages. Citric acid containing fruit is widely produced. Further, citrate is often listed as one of the top five ingredients in common lemon/lime flavored beverages. Citrate is also a relatively simple molecule, having three carboxylic acids emanating from a central carbon. Citrate's charge is minus three (near neutral pH) and therefore is distinctive compared to other possible interfering species present in beverages such as simple salts and sugars. Hence, if a receptor complementary to both the charge and hydrogen bonding ability of citrate were to be developed, potential interference from competing analytes would not be a concern in a food industry application.

Design principles such as preorganization, hydrogen bonding, and charge pairing may be tested within the context of achieving selective and strong binding of polycarboxylic anions in water. These are well accepted molecular recognition paradigms, but they have been utilized under different conditions than those used herein. For example, although the benefits of preorganization are documented (Lehn, *Supramolecular Chemistry, Concepts and Perspective*, VCH, New York, 1995; Cram, *Angew. Chem. Int. Ed. Engl.*, 27:1009, 1988), they have been mostly conducted in low dielectric media or with studies of hydrophobic interactions in water. Contradictory results are found for hydrogen bonding groups for phosphates and carboxylates in water. For instance, ammonium groups are more effective for charge pairing than guanidiniums due to the higher localization of charge (Dietrich et al., *Helv. Chem. Acta.*, 62:2763, 1979), yet nature exhibits a preference to use arginine rather than lysine to bind these anions, possibly due to an increase in the number of possible hydrogen bonds (Hannon et al., *Bioorganic Frontiers*, Springer Verlag, Berlin, 3:143–256, 1993). It is also generally found that the higher the charge on the host or guest the larger the binding constant (Dietrich, et al. *Helv. Chem. Acta.*, 62:2763, 1979). The field of molecular recognition is sophisticated enough that applications for rationally designed and totally synthetic receptors are realistic (Morttellaro and Nocera, *Chemtech*, 26:17, 1996; Diamond and McKervey, *Chem. Soc. Rev.*, 16, 1996). Although the field has primarily focused upon understanding non-covalent interactions such as hydrogen bonding and hydrophobic effects (Peterson et al., *Tetrahedron*, 51:401, 1995; Perreault et al., *Tetrahedron*, 51:353, 1995), recent effort has been put toward the development of sensors for various analytes. As a few examples, sensors for sugars (James et al., *Angew. Chem. Int. Ed. Engl.*, 33:2207, 1994), Zn(II) (Godwin and Berg, *J. Am. Chem. Soc.*, 118:6514, 1996), creatine (Bell et al., *Science*, 269:671–674, 1995), BTXs (Pikramenou et al., *Tetrahedron Lett.*, 34:3531, 1993) and cAMP (Adams et al., *Nature*, 349:694, 1991) have been developed. The promise of this field is highlighted by the recent establishment of a World Wide Web site soliciting sensors (http://www.curscl.co.uk/BioMedNet/cmb/cmbinf.html).

Analytes are sensed when they physically bind to a properly designed receptor and produce a measurable signal upon complexation (Fabbrizzi and Poggi, *Chem. Soc. Rev.*, 200, 1995). Therefore a successful sensor system will possess both a "host," developed via molecular recognition principles, and a vehicle for producing a signal. Spectroscopic or electrochemical changes as a function of the analyte have been the most popular vehicles for qualitative and quantitative assays. Although absorption spectroscopy and electrochemical changes are useful for certain applications, fluorescence spectroscopy offers advantages over these techniques (Czarnik, *Chemistry and Biology*, 2:423, 1995). Fluorescence emission appears at longer wavelengths than fluorescence excitation and the background signal is typically low, resulting in high sensitivity.

Figure 1:
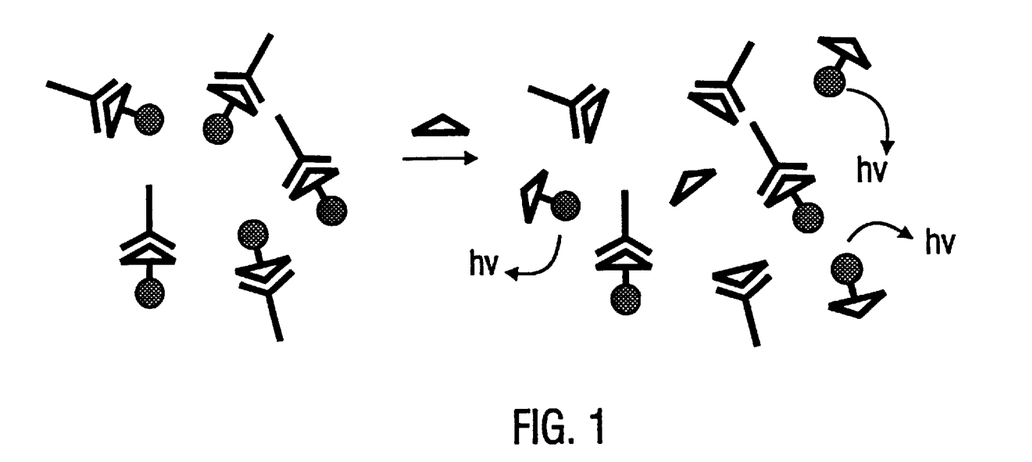
FIG. 1 depicts immunoassay technology in which a labeled antigen is released upon addition of an unlabeled antigen resulting in measurable spectroscopic change.

Using antibodies in a sensing scheme is well developed method for immunoassay technologies (Birch and Lennox, *Monoclonal Antibodies: Priciples and Applications*. John Wiley & Sons, New York, 1995). These assays typically rely on a competition approach. Addition of a solution to be analyzed containing an unlabeled antigen results in the release of a labeled antigen and hence a signal (FIG. 1, Birch and Lennox, *Monoclonal Antibodies: Priciples and Applications*. John Wiley & Sons, New York, 1995). This approach is particularly amenable to synthetic receptors, possibly resulting in sensors for a wide variety of analytes.

Polycarboxylic acids are frequently found in food products. Polycarboxylic acids include a wide variety of compounds containing at least two carboxylic acid groups. A number of polycarboxylic acids are present in food products including, but not limited to, maleic acid, ascorbic acid, and citric acid. In general it is desirable to design a variety of receptors for a variety of polycarboxylic acids. Such receptors would be useful for determining the concentration of some of polycarboxylic acids in food products.

SUMMARY OF THE INVENTION

An embodiment of the invention relates to a receptor for binding to polycarboxylic acids, the receptor having the general formula:

wherein X is selected from the group consisting of carbocyclic systems and $C_1$–$C_{10}$ alkanes. Each of $R^1$ independently represents —$(CH_2)_y$—$NR^3$—$C(NR^4)$—$NR^5$, or —$(CH_2)_y$—$NR^6R^7$, where y is an integer of at least 1; $R^3$, $R^4$, and $R^5$ independently represent hydrogen, alkyl, aryl, alkyl carbonyl of 1 to 10 carbon atoms, or alkoxy carbonyl of 1 to 10 carbon atoms, or $R^4$ and $R^5$ together represent a cycloalkyl group; $R^6$ represents hydrogen, alkyl, aryl, alkyl carbonyl of 1 to 10 carbon atoms, or alkoxy carbonyl of 1 to 10 carbon atoms; $R^7$ represents alkyl, aryl, alkyl carbonyl of 1 to 10 carbon atoms, or alkoxy carbonyl of 1 to 10 carbon atoms; and where $R^6$ and $R^7$ together represent a cycloalkyl group. Each of $R^2$ independently represents hydrogen, alkyl, alkenyl, alkynyl, phenyl, phenylalkyl, arylalkyl, aryl, or together with another $R^2$ group represent a carbocyclic ring.

An embodiment of the above-described receptor is preferably mixed with an indicator in a solvent to form a composition for determining the concentration of a polycarboxylic acid dissolved in a solution. The indicator is adapted to bind to the receptor. Binding of the indicator to the receptor may cause a number of physical properties of the receptor to change. The solvent preferably comprises water, a water soluble organic solvent, or a mixture thereof. When a polycarboxylic acid is added to the composition the polycarboxylic acid may interact with the receptor such that the indicator is released from the receptor.

In an embodiment the above-described composition may be used to determine the concentration of a polycarboxylic acid in a solution. Before addition of polycarboxylic acid to the composition, various physical properties of the composition, particularly of the indicator, are preferably measured. After addition of the polycarboxylic acid to the composition these physical properties are preferably remeasured, and the corresponding changes noted. Based on the degree of change in physical properties a concentration of the polycarboxylic acid may be determined.

An advantage of the present invention relates to the synthesis of a receptor which specifically binds polycarboxylic acids.

Another advantage of the present invention relates to the use of a receptor which specifically binds polycarboxylic acids in a composition for determining the concentration of a polycarboxylic acid in a solution.

BRIEF DESCRIPTION OF THE DRAWINGS

Further advantages of the present invention will become apparent to those skilled in the art with the benefit of the following detailed description of the preferred embodiments and upon reference to the accompanying drawings in which.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

Combining certain molecular recognition paradigms permitted the design of a particularly effective preorganized receptor, which is complementary to both the charge distribution and hydrogen bonding sites of polycarboxylic acids. The term "Polycarboxylic acids" within the context of this application is taken to mean a class of compounds which contain at least two carboxylic acid groups. The polycarboxylic acids may also include other functional groups. The receptor has been designed to preferably bind a variety of polycarboxylic acids. By modifying the structure of the receptor, the receptor may be made selective for a specific polycarboxylic acid in the presence of other polycarboxylic acids.

In an embodiment a receptor for binding to polycarboxylic acids has the general formula:

wherein X includes carbocyclic systems or $C_1$–$C_{10}$ alkanes. The subscripts n and m denote the number of groups corresponding to the general structures of $R^1$ and $R^2$, respectively. Preferably n is an integer of at least 2, m is an integer of at least 1. Each of $R^1$ independently represent —$(CH_2)_y$—$NR^3$—$C(NR^4)$—$NR^5$, or —$(CH_2)_y$—$NR^6R^7$, where y is an integer of at least 1 and where $R^3$, $R^4$, and $R^5$ independently represents hydrogen, alkyl, aryl, alkyl carbonyl of 1 to 10 carbon atoms, or alkoxy carbonyl of 1 to 10 carbon atoms, or $R^4$ and $R^5$ together represent a cycloalkyl group; $R^6$ represents hydrogen, alkyl, aryl, alkyl carbonyl of 1 to 10 carbon atoms, or alkoxy carbonyl of 1 to 10 carbon atoms; $R^7$ represents alkyl, aryl, alkyl carbonyl of 1 to 10 carbon atoms, or alkoxy carbonyl of 1 to 10 carbon atoms; $R^6$ and $R^7$ together represent a cycloalkyl group. Each of $R^2$ independently represents hydrogen, alkyl, alkenyl, alkynyl, phenyl, phenylalkyl, arylalkyl, aryl, or together with another $R^2$ group represent a carbocyclic ring.

As used herein, "alkyl" is intended to include branched, cyclic and straight-chain saturated aliphatic hydrocarbon groups. "Alkenyl" is intended to include hydrocarbon chains of either a straight, cyclic, or branched configuration and one or more unsaturated carbon-carbon bonds which may occur in any stable point along the chain. "Alkynyl" is intended to include hydrocarbon chains of either a straight, cyclic or branched configuration and one or more triple carbon-carbon bonds which may occur in any stable point along the chain. "Cycloalkyl" is intended to include saturated ring groups, including mono-, bi-, or poly-cyclic ring systems, such as cyclopropyl, cyclobutyl, cyclopentyl, cyclohexyl, cycloheptyl, adamantyl, and cyclooctyl. "Alkyl carbonyl" is intended to include an alkyl group of an indicated number of carbon atoms attached through a carbonyl group to the residue of the compound at the designated location. "Alkoxy carbonyl" is intended to include an alkoxy group of an indicated number of carbon atoms attached through a carbonyl group to the residue of the compound at the designated location. "Phenyl" is intended to include a benzene ring attached to the residue of the compound at the designated location. "Aryl" is taken to include substituted aromatic ring systems, where the rings may be substituted with hydrogen, alkyl, alkenyl, alkynyl, cycolalkyl, alkyl carbonyl, alkoxy carbonyl, halogens, halogenated alkyl groups, and groups represented by the formulas —OR, —SR, —NR'R", —$CO_2R$ where R is hydrogen, alkyl or aryl, —$NO_2$, —CN, —SCN. "Aryl($C_1$-$C_4$ alkyl)" is intended to include an aryl group attached through a $C_1$-$C_4$ alkyl group to the residue of the compound at the designated location. "Carbocyclic" is intended to mean any stable 3 to 8 membered monocyclic or bicyclic ring system, or 7 to 14 membered bicyclic or tricyclic ring system, or up to 26 membered polycyclic carbon ring, any of which may be saturated (such as cyclohexyl), partially unsaturated (such as cyclohexenyl), or aromatic. Examples of such carbocycles include, but are not limited to, cyclopropyl, cyclopentyl, cyclohexyl, phenyl, biphenyl, naphthyl, indanyl, and adamantyl.

Figure 2:
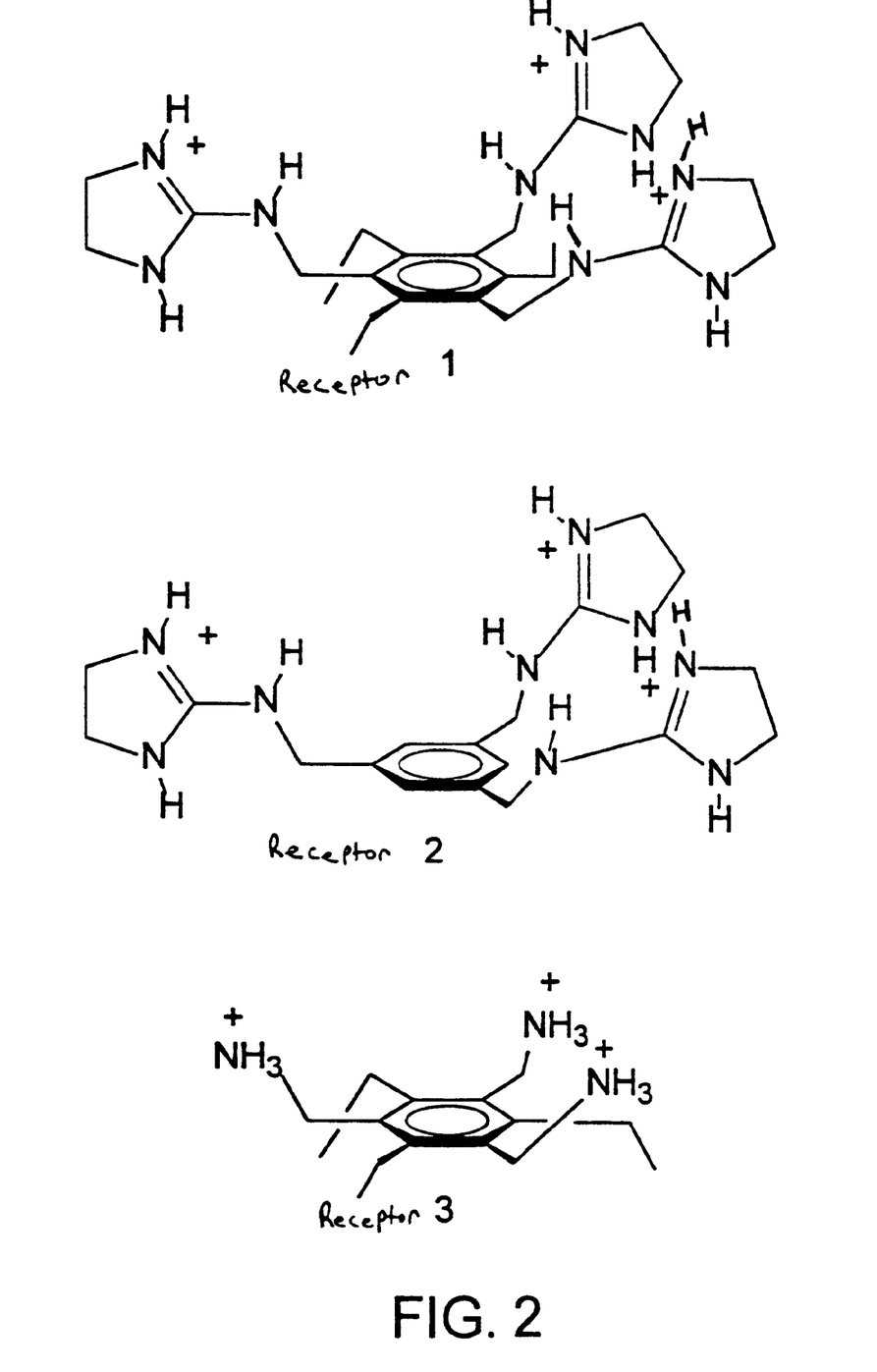
FIG. 2 depicts a structure of receptor 1, receptor 2 and receptor 3.

In an embodiment a receptor preferably comprises guanidinium groups or amino groups positioned about a benzene ring. Examples of such a receptor include, but are not limited to receptor 1, receptor 2, and receptor 3 as depicted in FIG. 2. The guanidinium group, embedded in an aminoimidazolinium group, is an efficient binding motif for carboxylic acids, resulting in binding constants of $10^1$ to $10^4$ M for host-guest complexes in highly competitive solvents such as DMSO or methanol (Fan et al., *J. Am. Chem. Soc.*, 115:369, 1993; Berger and Schmidtchen, *J. Am. Chem. Soc.*, 118:8947, 1996; Schiessl and Schmidtchen, *Tetrahedron Letts.*, 34:2449, 1993; Albert et al., *J. Am. Chem. Soc.*, 117:1143, 1995).

In general receptors may be synthesized from a variety of structures containing at least two alkylhalide groups having the general structure Base-$[(CH_2)_yZ]_n$ where Base is a base structure upon which the receptor is built. An alkylhalide group is represented by —$[(CH_2)_yZ]_n$ where y is an integer of at least 1, where n is an integer of at least 2 and Z is a halogen, sulfonate, or alcohol. A variety of base structures may be used to synthesize the receptor. In the above embodiment the base structure is preferably a benzene ring. In other embodiments any of a variety of carbocyclic ring systems may be used, including, but not limited to, cyclopropane, cyclobutane, cyclopentane, cyclohexane, napthalene, and anthracene. The base structure may also be a non-cyclic alkane chain. In a preferred embodiment the base structure is preferably a carbocyclic ring system. In another preferred embodiment the base structure is preferably an $C_1$–$C_{10}$ alkane. The synthesis of receptors using these base structures may be accomplished by modifications of the synthetic scheme for the synthesis of receptors 1 and receptor 3 shown in FIG. 3.

The base structures may include a number of substituents in addition to the required alkylhalides. In general the base structure may include any number of groups independently represented by hydrogen, alkyl, alkenyl, alkynyl, phenyl, phenylalkyl, arylalkyl, aryl, or together with another such group represent a carbocyclic ring.

Figure 3:
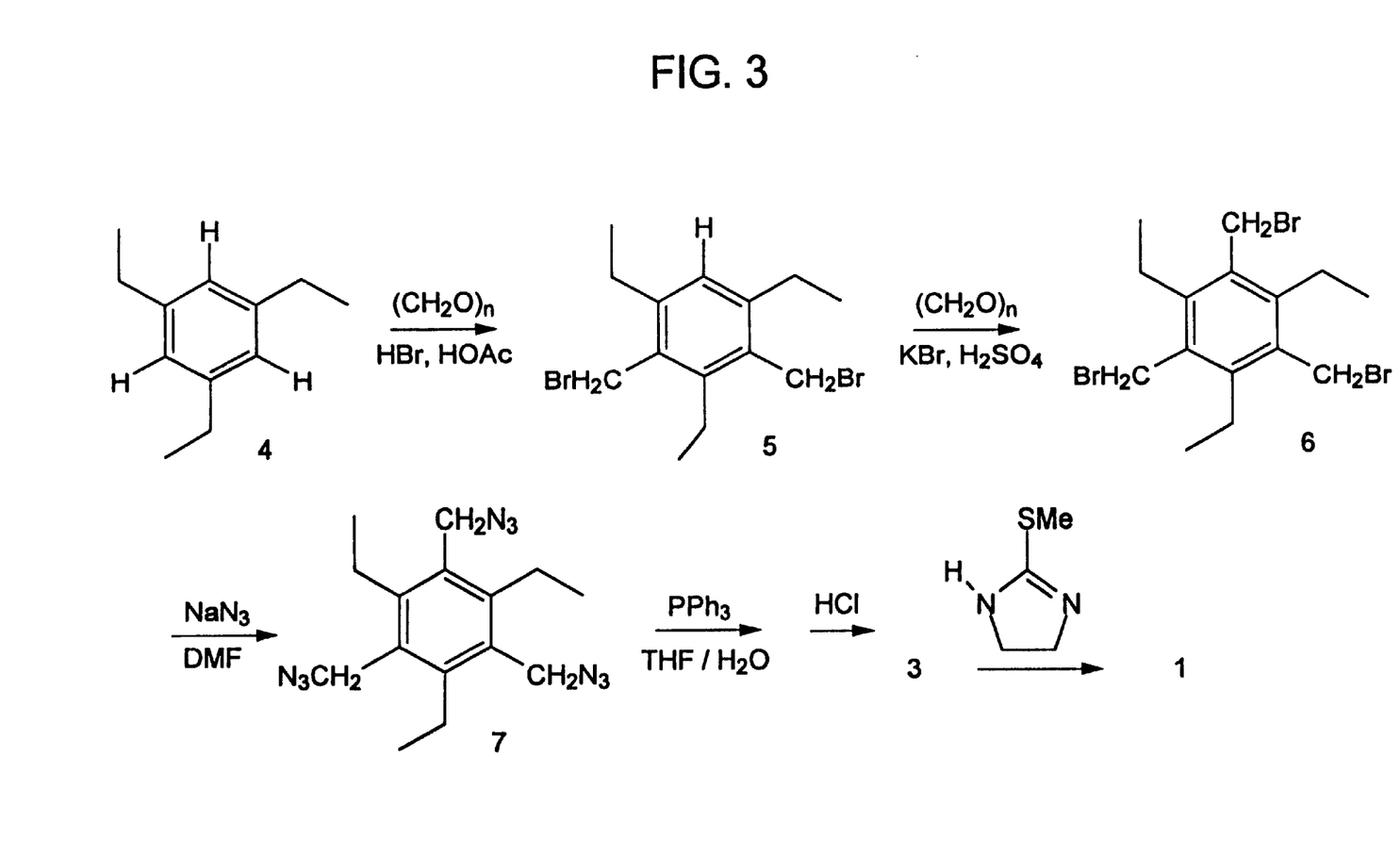
FIG. 3 depicts a synthesis of receptor 1 and receptor 3.

In an embodiment the alkylhalides residing on a base structure as described above may be converted into amine groups as depicted in FIG. 3. In general reaction of the alkylhalides residing on a base structure as described above with (1) $NaN_3$/DMF, (2) $PPh_3$/THF/$H_2O$, and (3) HCl will convert the alkylhalide into an alkylamine of structure —$(CH_2)_yNH_2$ where y is an integer of at least 1. The guanidinium groups of structure —$(CH_2)_y$—$NR^3$—C($NR^4$)—$NR^5$ may be synthesized by reacting an alkylamine of a structure —$(CH_2)_yNH_2$ with a variety of isothioureas, where $R^3$, $R^4$, and $R^5$ may be independently represented by hydrogen, alkyl, aryl, alkyl carbonyl of 1 to 10 carbon atoms, or alkoxy carbonyl of 1 to 10 carbon atoms, or $R^4$ and $R^5$ together represent a cycloalkyl group. It should be appreciated that the amino group may readily converted into a number of derivatives of the form —$(CH_2)_yNR^6R^7$ where $R^6$, and $R^7$ independently represents hydrogen, alkyl, aryl, alkyl carbonyl of 1 to 10 carbon atoms, or alkoxy carbonyl of 1 to 10 carbon atoms, or $R^6$ and $R^7$ together represent a cycloalkyl group.

Figure 5:
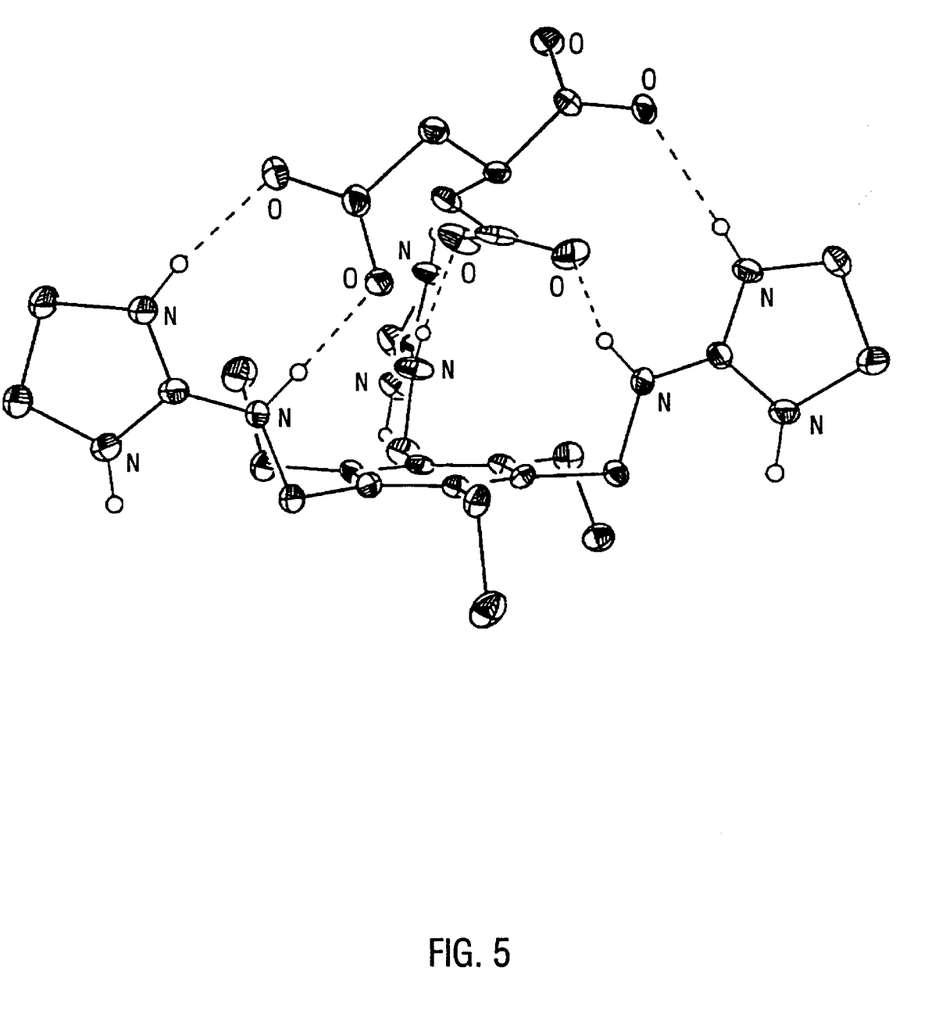
FIG. 5 depicts an x-ray crystal structure of receptor 1 and tricarballate bound together in a first orientation.
Figure 6:
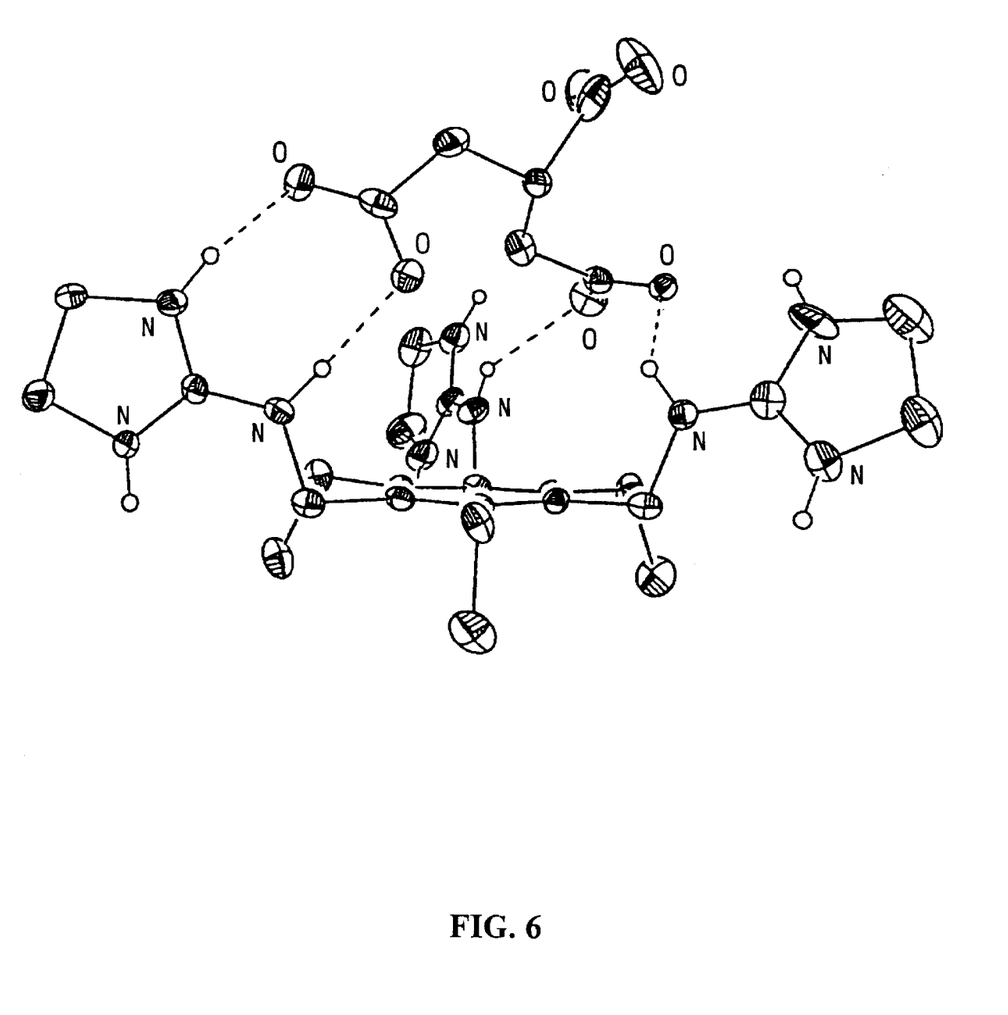
FIG. 6 depicts an x-ray crystal structure of receptor 1 and tricarballate bound together in a second orientation.

FIG. 5 and FIG. 6 depict X-ray crystal structures of a receptor (receptor 1) with a polycarboxylic acid (tricarballate). The X-ray crystal structure confirms the presence of hydrogen bonds and ion pairs in the host guest complex. However, two different complexes were found in the unit cell (FIG. 5 and FIG. 6). All carboxylates in both structures, with the exception of one, make contact with the guanidinium groups. The exception is the carboxylate shown pointing up in structure FIG. 6. The unbound carboxylate depicted in FIG. 6 instead hydrogen bonds to two methanols which in turn hydrogen bond to guanidiniums. The structure in FIG. 5 has one ethyl group oriented on the same face of the benzene ring as the guanidinium groups. This is not likely to be the thermodynamically favored conformation in solution (Kilway and Siegel, 1992). Close examination of the crystal packing reveals the reason for this unexpected conformation. The guanidiniums next to this ethyl group tend to make short hydrogen bonds (2.54 A) to carboxylates of the bound polycarboxylic acid. This tends to orient a guanidinium group close to the ethyl group forcing it to rotate into the conformation found.

In an embodiment the receptor may be used in conjunction with an indicator to determine, qualitatively and quantitatively, the presence of a polycarboxylic acid in a solution. In another embodiment the mixture of receptor and indicator may be used to determine, qualitatively and quantitatively, the concentration of a polycarboxylic acid in a solution containing at least one other component. The other component may be a salt, sugar, monocarboxylic acid, or a different polycarboxylic acid. In general the indicator may be any compound that may bind to the receptor.

The indicator preferably has a variety of physical properties which may be measured. These physical properties include, but are not limited to, ultraviolet absorption, visible absorption, infrared absorption, fluorescence, and magnetic resonance. Preferably the indicator is a dye having either a strong fluorescence, a strong ultraviolet absorption, a strong visible absorption or a combination of these physical properties. Examples of indicators include but are not limited to 5-carboxyfluorescein and ethidium bromide. When the indicator is mixed with the receptor, the receptor and indicator interact with each other such that the above mentioned physical properties of the indicator, as well as other physical properties may be altered. The nature of this interaction is preferably a binding interaction, wherein the indicator and receptor are attracted to each with a sufficient force to allow the newly formed receptor-indicator complex to function as a single unit. The binding of the indicator and receptor to each other may take the form of a covalent bond, an ionic bond, a hydrogen bond, a van der Waals interaction, or a combination of these bonds.

In a preferred embodiment the indicator is chosen such that the binding strength of the indicator to the receptor is less than the binding strength of the a polycarboxylic acid to the receptor. Thus, in the presence of a polycarboxylic acid the binding of the indicator with the receptor may be disrupted by the presence of a polycarboxylic acid releasing the indicator from the receptor. When released, the physical properties of the indicator are preferably altered from those it exhibited when bound to the receptor. The indicator may revert back to its original structure, thus regaining its original physical properties.

The above system may be used to determine, in a qualitative or quantitative manner, the concentration of polycarboxylic acid in solution. Alternatively, the system may be used to determine the concentration of polycarboxylic acid in solution containing other components. These other components may include, but are not limited to salts, sugars, monocarboxylic acids, or other polycarboxylic acids. In an embodiment the receptor and indicator are mixed together in a solvent to form a receptor-indictor complex. The pH of the composition may be altered to a value of at least 5.0. The pH of the solution is altered such that the polycarboxylic acid may be substantially ionized when mixed with the composition. After measuring the physical properties of this receptor-indicator complex, a solution containing a polycarboxylic acid is preferably added to the mixture. The pH of the solution may be altered to a value of at least 5.0 prior to adding to the solution. The pH of the solution is altered such that the polycarboxylic acid may be substantially ionized. Addition of the polycarboxylic acid preferably causes disruption of the receptor-indicator complex such that the indicator is released from the receptor. Measurement of the physical properties of the resulting mixture may allow the qualitative and/or quantitative determination of the amount of polycarboxylic acid in a solution.

The receptor and indicator are preferably mixed together in a solvent. Many indicators are sensitive to the pH of the solvent. It may be necessary to adjust the pH of the solvent, when the solvent comprises water, in order to maximize interaction of the indicator with the receptor. The solvent may be water, a water soluble organic solvent, or a mixture thereof. Examples of water soluble organic solvents include, but are not limited to THF, acetonitrile, DMF, dioxane, alcohols, and DMSO. A buffering agent may be added to the solvent. The buffering agent preferably controls the pH of the composition of receptor and indicator during use. The buffering agent is preferably chosen such that the interaction of the buffering agent with the receptor is minimized. The buffering agent may include, but is not limited to HEPES (4-(2-hydroxyethyl)-1-piperazineethanesulfonic acid), borate salts, TRIS (tris(hydroxymethyl)aminomethane), or bicarbonate salt. The water soluble organic solvent preferably helps inhibit the interaction of a buffering agent with the receptor.

EXAMPLES

1. Synthesis of receptor 1, receptor 2 and receptor 3

The synthesis of receptor 1 and receptor 3 is depicted in FIG. 3. Receptor 1 was synthesized via the reaction of receptor 3 with S-methylthio-2-imidazoline (Metzger et al., *Synthesis*, 565, 1995; which is incorporated by reference as if fully set forth herein). Although a synthesis of receptor 3 was documented, (Stack et al., *J. Am. Chem. Soc.*, 115:6466, 1993) it involved hydrogenation of 1,3,5-tricyano-2,4.6-triethylbcnzene, a step difficult to perform on a scale greater than 1 g. Therefore the route shown in FIG. 3 was developed. Initially bromomethylation of 1,3,5-triethylbenzene (4) yielded compound 6 in greater than 53% yield over two steps. Compound 6 may be synthesized in one step, but to simplify purification problems this two step sequence may be used. The bromines were then converted by sodium azide in DMF to the azide (compound 7). Finally reduction of the azide 7 with triphenylphosphine ' in THF/water gave the triamine, receptor 3. Receptor 3 was converted into receptor 1 by reaction of receptor 3 with S-methylthio-2-imidazoline. Receptor 2 was synthesized from S-methylthio-2-imidazoline and 1,3,5-triaminomethylbenzene (Weitl and Raymond, *J. Am. Chem. Soc.* 91:2728, 1979).

2. Effect of Solvent on Binding of Receptor 1 With Trisodium Citrate

The complexation of trisodium citrate by receptor 1 was studied by $^1$H NMR spectroscopy. Binding constants were obtained by $^1$H NMR titration techniques as set forth in Conners, *Binding Constants, The Measurement of Molecular Complex Stability*, John Wiley & Sons; New York, 1987; (which is incorporated by reference as if fully set forth herein), followed by computer fitting of the experimental isotherm using the typical 1:1 binding algorithm (Wilcox and Cowart, *Tetrahedron Lett.*, 27:5563, 1986). To explore the effect of buffer on complexation strength, binding constants were determined with added phosphate and HEPES buffers (Table 1). A phosphate buffer inhibited citrate binding, due to the relatively high concentration of the buffer compared to citrate. Even buffers such as HEPES, containing sulfonate groups known for their weak interaction with guanidinium groups, decreased the binding of receptor 1 to citrate, but with less impact. Addition of organic solvents to buffered solutions favored the complexation of the phosphate buffer and decreased the binding constant for citrate. The binding constants remained unchanged, within the experimental error, when HEPES buffer was used and the ratio of organic solvent was increased. This effect demonstrates the better binding properties of guanidiniums for phosphates versus sulfonates. Table I shows binding constants of Receptor 1 with trisodium citrate in various solvent systems and with two different buffers.

TABLE I

| Buffer | Solvent System | Binding Constant $M^{-1}$ |
| --- | --- | --- |
| Phosphate | 100% $D_2O$ | $1.2 \times 10^2$ |
| Phosphate | 80% $D_2O$/20% $CD_3CN$ | 41 |
| Phosphate | 60% $D_2O$/40% $CD_3CN$ | 24 |
| HEPES | 100% $D_2O$ | $2.0 \times 10^2$ |
| HEPES | 80% $D_2O$/20% $CD_3CN$ | $1.8 \times 10^2$ |
| HEPES | 60% $D_2O$/40% $CD_3CN$ | $2.1 \times 10^2$ |
| HEPES | 40% $D_2O$/60% $CD_3CN$ | $2.1 \times 10^2$ |

3. Binding of Receptor 1 with various mono and polycarboxylic acids

Figure 4:
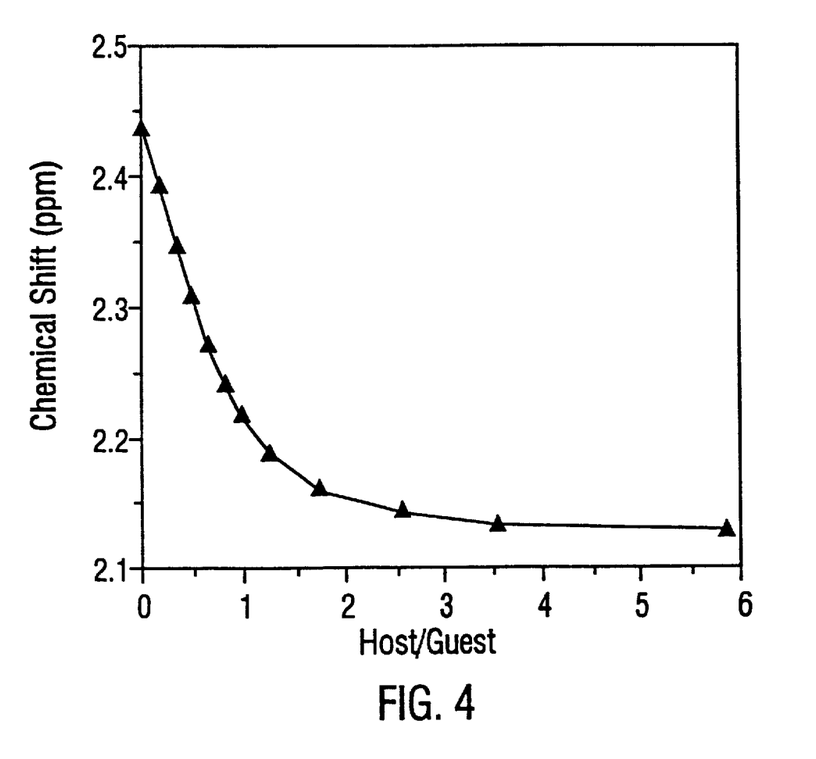
FIG. 4 depicts a binding isotherm with receptor 1 wherein the data points are from a $^1$H NMR analysis of a titration in $D_2O$.
Figure 7:
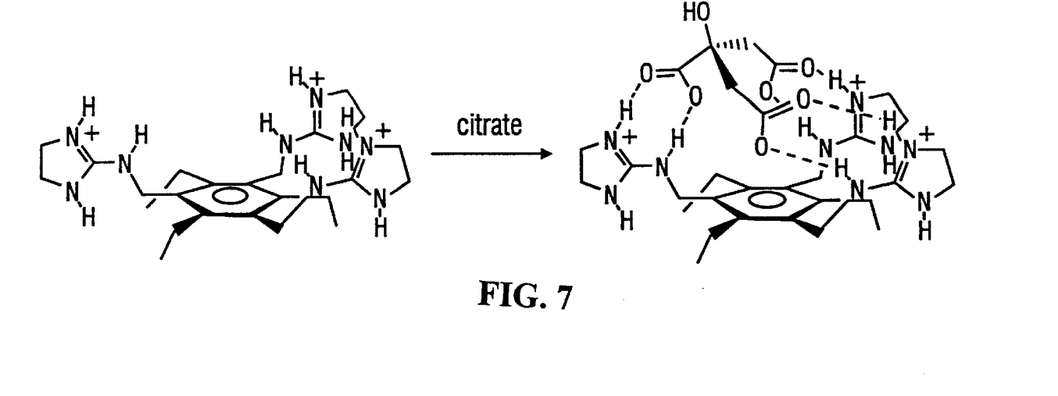
FIG. 7 depicts a possible structure of receptor 1 bound to citrate.

Both the tricarboxylic acids citrate and tricarballate bind with receptor 1 to yield binding constants near $7 \times 10^3$ $M^{-1}$ in pure water (Table 2, FIG. 4, and FIG. 7). These guests give the largest binding constants obtained in these studies. Even anions with greater charge, such as with $ATPA^{-4}$, did not result in stronger complexation, indicating the complementarity between receptor 1 and citrate. Smaller binding constants for succinate and glutarate were found (both near $2 \times 10^2$ $M^{-1}$). Acetate showed very weak binding (estimated to be <10 $M^{-1}$), but the binding isotherm indicated equilibria beyond simple one to one association. Neither adenosine triphosphate, uridine monophosphate (3'-UP) nor its cyclic analog, cyclic-2,3-UP, had significant affinity for receptor 1.

TABLE 2

| Host | Guest | Binding Constant $M^{-1}$ |
| --- | --- | --- |
| Receptor 1 | Citrate | $6.9 \times 10^3$ |
| Receptor 1 | Tricarballate | $7.3 \times 10^3$ |
| Receptor 1 | Succinate | $2.1 \times 10^2$ |
| Receptor 1 | Glutarate | $2.2 \times 10^2$ |
| Receptor 1 | Acetate | <10 |
| Receptor 1 | Phosphate, pH 7.4 | $5 \times 10^1$ |
| Receptor 1 | $ATP^{-4}$ | $1.2 \times 10^2$ |
| Receptor 1 | 3'-UP | $2.1 \times 10^2$ |
| Receptor 1 | cyclic-2,3-UP | <10 |
| Receptor 3 | Citrate | $3.0 \times 10^3$ |
| Receptor 2 | Citrate | $2.4 \times 10^3$ |

4. Determination of the Concentration of Citrate in a Solution

Figure 8:
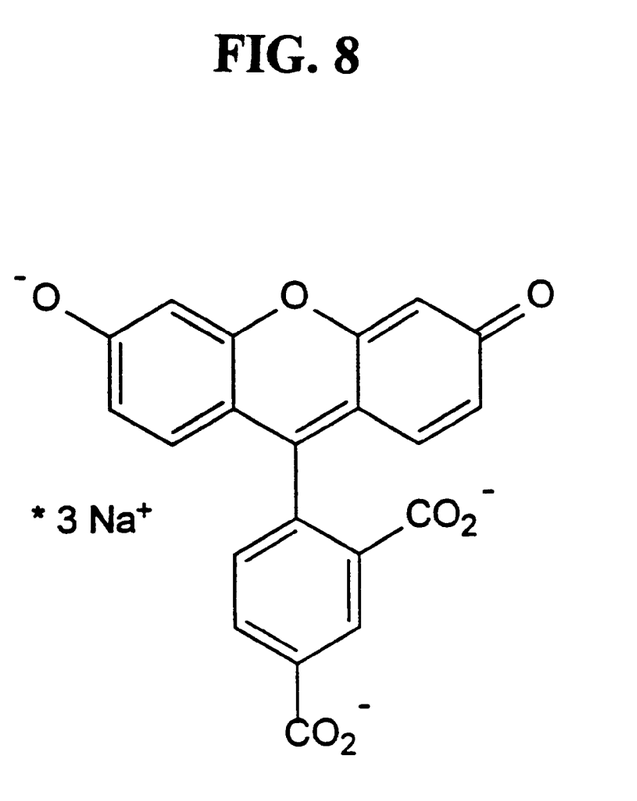
FIG. 8 depicts structure of 5-carboxyfluorescein.

The present sensing strategy relied upon using 5-carboxyfluorescein (FIG. 8), a fluorescent/colorimetric probe, to produce a spectroscopic signal upon its replacement by citrate in the host guest complex. This probe was chosen since it is commercially available, it is relatively inexpensive, it possesses two carboxylates for binding with receptor 1, and only very small quantities proved to be necessary. The spectroscopy of 5-carboxyfluorescein is sensitive to pH changes, and therefore a buffer to maintain constant pH was necessary in the sensing studies (Bramhall et al., *Biochem.*, 26:6330, 1987; Graber et al., *Anal. Biochem.*, 156:202, 1986). A charged buffer may act as a competitor with the polycarboxylic acid for the binding sites on the receptor. In order to compensate for this effect and to enhance the binding, methanol was added to the buffered solutions. After several trial studies were performed, 25% water in methanol (15 mM HEPES buffer at pH 7.4) was found to be the most advantageous solvent system. UV/vis spectroscopy was employed to give a binding constant of $4.7 \times 10^3$ $M^{-1}$ of receptor 1 with 5-carboxyfluorescein under the conditions of the inventors sensing assay, using the Benesi-Hildebrandt method (Benesi and Hildebrandt, *J. Am. Chem Soc.*, 71:2703, 1949; Diederich et al. *J. Am. Chem. Soc.*, 108:2273, 1986, both of which are incorporated by reference as if fully set forth herein). In the same system a binding constant of $2.9 \times 10^5$ $M^{-1}$ was determined for citrate and receptor 1 with a competition assay, in which citrate is added to a solution of Receptor 1 and 5-carboxyfluorescein, and the change in absorbance is monitored (Conners, *Binding Constants, The Measurement of Molecular Complex Stability*, John Wiley & Sons; New York, 1987). This binding constant is among the largest values yet reported for the recognition of anions in highly aqueous media and is certainly of a magnitude appropriate for sensing citrate at mM and $\mu$M concentrations.

5. Binding Constant of Receptor 1 to 5-Carboxyfluorescein

Figure 9:
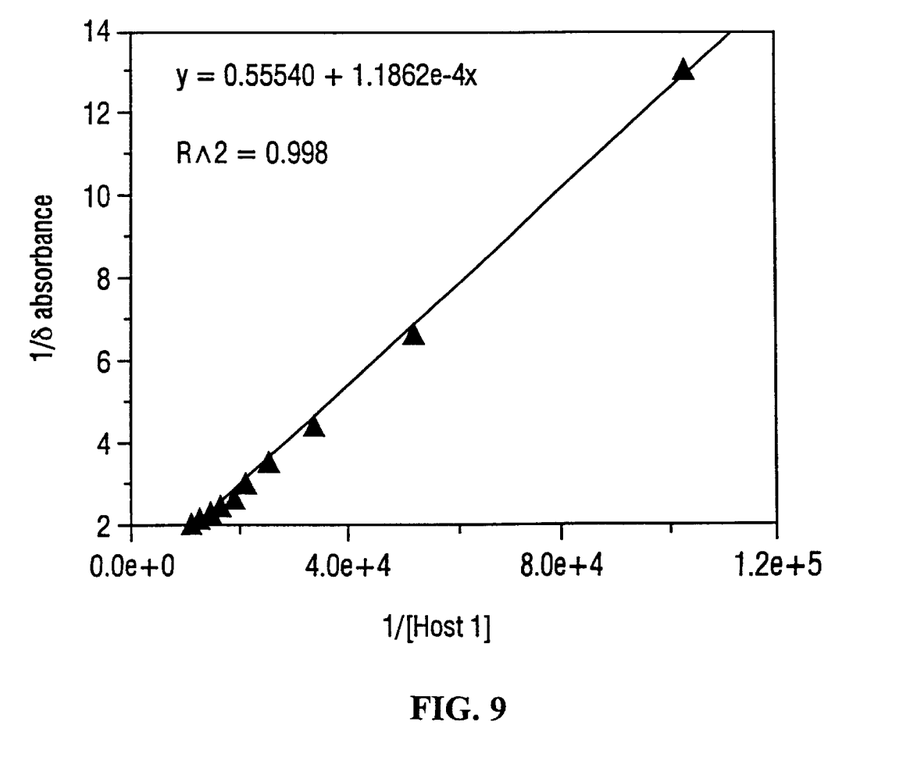
FIG. 9 depicts a plot of data collected using the Benesi-Hildebrandt method to determine a binding constant of receptor 1 and 5-carboxyfluorescein in 75% methanol, 25% water and 5 mm HEPES, pH 7.4.

The Benesi-Hildebrand method was used to determine the binding constant of receptor 1 and 5-carboxyfluorescein in 75% methanol, 25% water, 5 mM HEPES buffer at pH 7.4. A plot of the 1/[concentration of host] vs. 1/[change in absobance] gives a straight line. See FIG. 9. From the slope and intercept of the curve a binding constant of $4.7 \times 10^3$ $M^{-1}$ was calculated.

6. Interaction of Citrate with Receptor 1 and 5-Carboxyfluorescein

Figure 10:
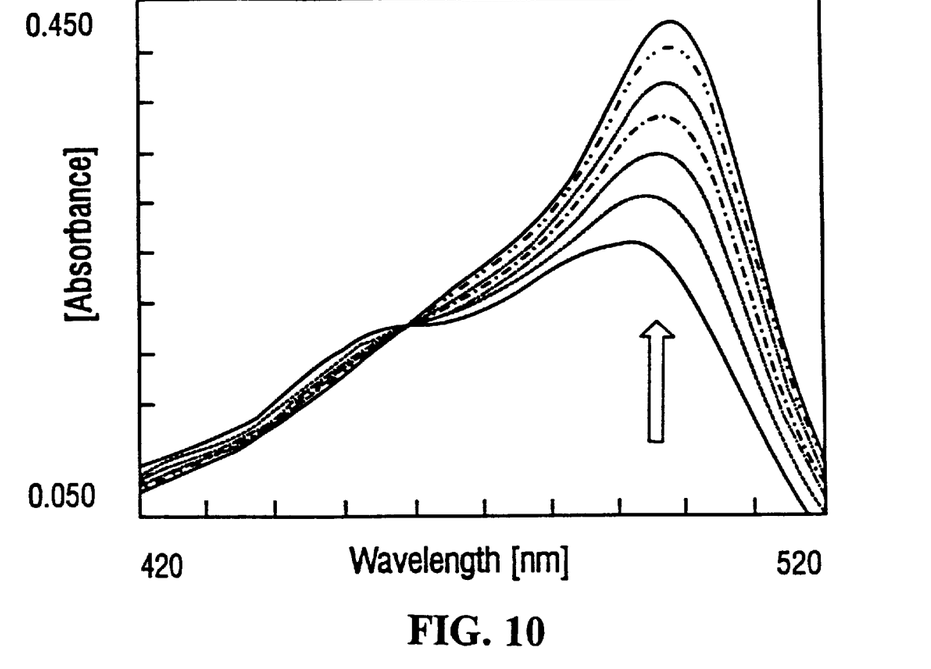
FIG. 10 depicts an ultraviolet spectrum of 5-carboxyfluorescein. The addition of receptor 1 caused an increase of the absorption. The lowest curve in FIG. 10 is 5-carboxyfluorescein in the absence of receptor 1.
Figure 11:
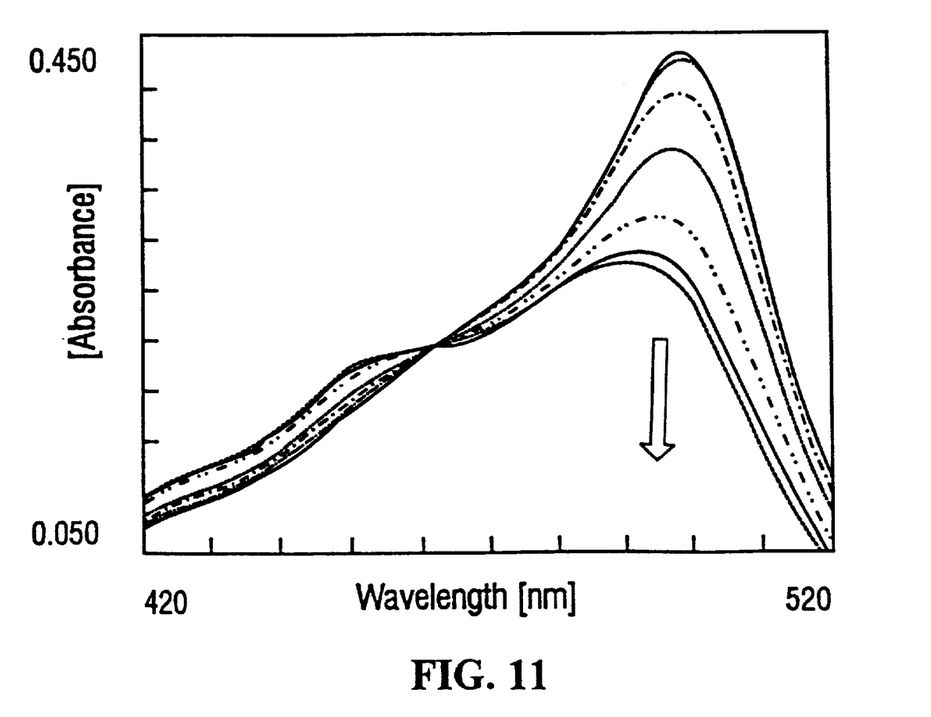
FIG. 11 depicts an ultraviolet absorption spectrum of 5-carboxyfluorescein. The addition of citrate to the 5-carboxyfluorescein/receptor 1 composition caused a decrease in the absorption.

The interaction of Citrate with receptor 1 and 5-carboxyfluorescein was studied in 75% methanol, 25% water, 5 mM HEPES buffer at pH 7.4. FIG. 10 depicts a series of UV spectroscopy curves taken after sequential additions of receptor 1. As shown in FIG. 10, the intensity of both fluorescence and absorbance increases with addition of receptor 1 to a constant concentration of 5-carboxyfluorescein, whereas it decreases upon addition of citrate to a constant concentration of receptor 1 and 5-carboxyfluorescein (see FIG. 11). This decrease results from an increase in the third $pK_a$ (that of the phenol moiety) of 5-carboxyfluorescein when unbound versus bound. Addition of succinate to the sensing ensemble resulted in small spectroscopic changes, but the addition of acetate, salt, or sugar resulted in essentially no changes. Therefore common contaminants present in beverages (e.g. maleate, ascorbate, lactate or benzoate) do not effect the inventors' sensing assay. This system shows how the structure of the receptor may be adjusted such that the receptor sensor is specific for specific polycarboxylic acids. In the above example receptor 1 is specific for tricarboxvlate structures, and therefore citrate is the only species which produces a significant signal.

7. Determination of Citrate in Beverages

Figure 12:
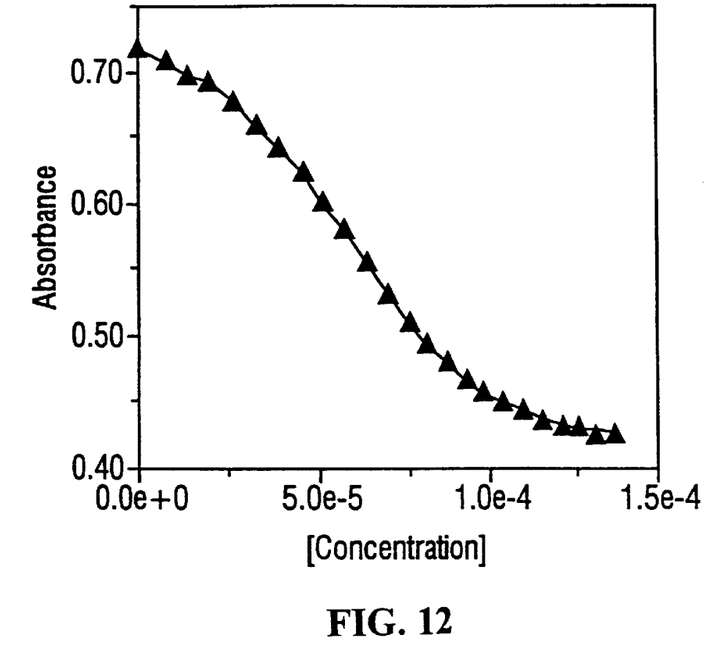
FIG. 12 depicts calibration curves utilized for the sensor assay where the addition of citrate to the 5-carboxyfluorescein/receptor 1 composition alters the ultraviolet absorbance of 5-carboxyfluorescein.
Figure 13:
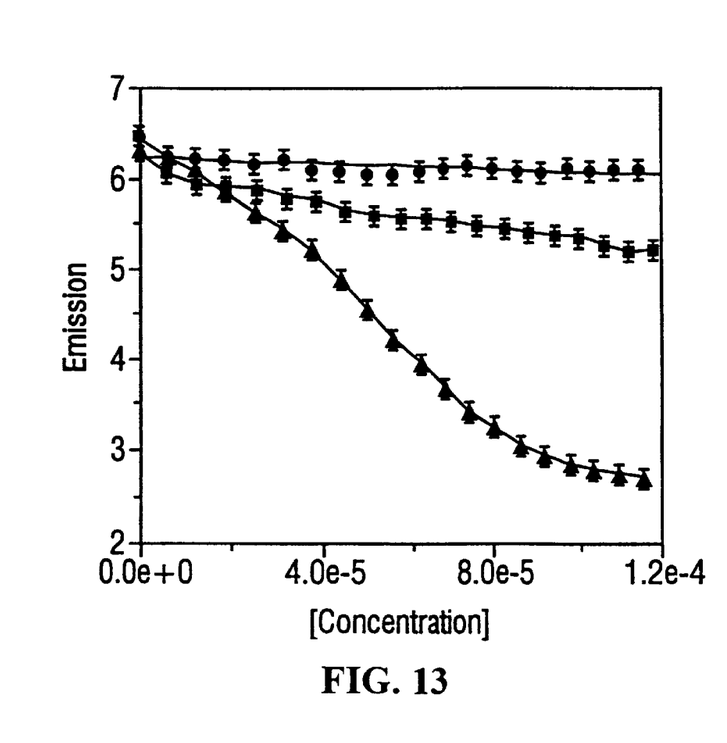
FIG. 13 indicates fluorescence calibration curves for 5-carboxyfluorescein fluorescence as effected by the addition of citrate, succinate and acetate.

A sensing composition is prepared such that receptor 1 has a concentration of 94 $\mu$M and 5-carboxyfluorescein has a concentration of 18 $\mu$M in 75% methanol, 25% water, 5 mM HEPES buffer at pH 7.4. Calibration curves for determining the concentration of citrate were generated by incrementally adding a 1.33 mM solution of citrate to the sensing composition. As citrate is added, i.e as the concentration of citrate is increased, the absorption drops as depicted in FIG. 12. This curve allows the determination of the concentration of citrate present based on the absorption value of the solution being tested. Additionally the same experiment may be performed using fluorescence to monitor the change in emission. As citrate is added, i.e as the concentration of citrate is increased, the emission drops as depicted in FIG.

13, bottom line (▲). The change in fluorescence is very small when succinate (■) or acetate (●) is added.

Determining the concentration of citrate in a large number of beverages was accomplished by adding up to 100 μL quantities of the beverage to the sensing ensemble (All beverages were filtered if necessary and pH adjusted to 7.4. and not more than 5% percent of volume change was allowed for each measurement) followed by determining the absorption or fluorescence, and reading the concentration off the calibration curves. The results for several drinks are given in Table 3. The system used for UV/vis spectroscopy consisted of 5 mM HEPES buffer, 94 μM receptor 1, 18 μM 5-carboxyfluorescein in 25% water and 75% methanol. All solutions were adjusted to pH 7.4 before methanol was added. A 1.33 mM solution of citrate in this composition was used for the calibration curves. The composition used for fluorescence spectroscopy was the same as for UV/vis spectroscopy except that a 84 μM receptor 1 and 5 μM 5-carboxyfluorescein were used. To verify that the method was working, known concentration of citrate were tested, and an NMR technique (as described previously) for measuring citrate was also used. All measurements agree with each other within less than 10 percent error with the exception of tests for Fresca and Mountain Dew. In these tests the NMR results differed by greater than 10% over the UV or Fluorescence methods. Additionally this method may be easily adapted to produce even more accurate results for any food industry application when the nature of contaminants is known. Table 3 shows concentrations of citrate in mM in the beverages determined by NMR, UV spectroscopy and fluorescence.

TABLE 3

|  | Concentration Citrate in mM by NMR | Concentration Citrate in mM by UV | Concentration Citrate in mM by Fluorescence |
| --- | --- | --- | --- |
| Citrate Model Sol. | — | 30.3 | 29.9 |
| Calibration Solution | — | 1.205 | 1.39 |
| Orange Juice | 43.1 | 44.1 | 44.7 |
| GATORADE | 15.95 | 15.05 | 15.1 |
| POWERADE | 12.4 | 11.1 | 11.3 |
| ALLSPORT | 7.4 | 7.1 | 8.1 |
| MOUNTAIN DEW | 7.95 | 5.5 | 5.4 |
| Tonic Water | 21.0 | 21.15 | 20.8 |
| FRESCA | 14.85 | 10.3 | 10.4 |
| COCA COLA | 0 | 0 | <0.5 |
| DIET COKE | 2.0 | <0.4 | <0.7 |
| PEPSI COLA | <0.6 | 0 | <0.8 |
| DIET PEPSI | 0.4 | 0 | <0.6 |

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A method for determining a concentration of a polycarboxylic acid in a solution, the method comprising:

adding the solution comprising the polycarboxylic acid to a composition, the composition comprising a receptor for the polycarboxylic acid, an indicator, and a solvent, the receptor being adapted to bind to the polycarboxylic acid during use, the indicator being adapted to bind to the receptor such that at least one physical property of the indicator are altered during use, wherein the receptor comprises a compound of the formula:

wherein X comprises carbocyclic systems or C1–C10 alkanes, n is an integer of at least 2, m is an integer of at least 1; and wherein each of $R^1$ independently represents —$(CH2)_y$—$NR^3$—$C(NR^4)$—$NR^5$, or —$(CH_2)_y$—$NR^6R^7$;

where y is an integer of at least 1;

where $R^3$, $R^4$, and $R^5$ independently represent hydrogen, alkyl, aryl, alkyl carbonyl of 1 to 10 carbon atoms, or alkoxy carbonyl of 1 to 10 carbon atoms, or $R^4$ and $R^5$ together represent a cycloalkyl group, where $R^6$ represents hydrogen, alkyl, aryl, alkyl carbonyl of 1 to 10 carbon atoms, or alkoxy carbonyl of 1 to 10 carbon atoms; where $R^7$ represents hydrogen, alkyl, aryl, alkyl carbonyl of 1 o 10 carbon atoms, or alkoxy carbonyl of 1 to 10 carbon atoms; or where $R^6$ and $R^7$ together represent a cycloalkyl group; and wherein each of $R^2$ independently represents hydrogen, alkyl, alkenyl, alkynyl, phelnyl, phenylalkyl, arylalkyl aryl, or together with another group represent a carbocyclic ring; and wherein n is at least equal to the number of carboxylic acid groups of the polycarboxylic acid;

allowing the polycarboxylic acid to interact with the receptor to substantially release the indicator from the receptors;

moitoring the change in the physical property of the indicator after the addition of the solution; and calculating the concentration of the polycarboxylic acid in the solution based on the change in physical property of the indicator.

2. The method of claim 1, wherein monitoring the change in the physical property of the indicator comprises measuring, the change in absorption of the composition.

3. The method of claim 1, wherein monitoring the change in the physical property of the indicator comprises measuring the fluorescence of the composition.

4. The method of claim 1, wherein monitoring the change in the physical property of the indicator comprises measuring the absorption of the composition, and monitoring the change in the physical property of the indicator comprises measuring the fluorescence of the composition.

5. The method of claim 1, wherein the solution of the polycarboxylic acid is filtered prior to adding the solution to the composition.

6. The method of claim 1, further comprising adjusting the pH of the solution of the polycarboxylic acid to a value of at least 5.0 prior to adding the solution to the composition.

7. The method of claim 1, further comprising adjusting the pH of the solution of the polycarboxylic acid to a value of at least 5.0 prior to adding the solution to the composition, and wherein the solution of the polycarboxylic acid is filtered prior to adding the solution to the composition.

8. The method of claim 1, wherein a binding strength of the receptor to the indicator is less than a binding strength of the receptor to the polycarboxylic acid.

9. The method of claim 1 wherein the receptor comprises a compound of the general formula:

$(R^1)_n$—X—$(R^2)_m$ wherein X is a benzene ring, n is an integer of at least 3, m is an integer of 1 to 3;

wherein each of $R^1$ independently represents —$(CH_2)_y$—$NR^3$—$C(NR^4)$—$NR^5$;

where y is an integer of 1 to 10;

where $R^3$, $R^4$, and $R^5$ independently represents hydrogen, alkyl, aryl, alkyl carbonyl of 1 to 10 carbon atoms, or alkoxy carbonyl of 1 to 10 carbon atoms, or $R^4$ and $R^5$ together represent a cycloalkyl group; and wherein each of $R^2$ independently represents hydrogen, alkyl, alkenyl, or alkynyl.

10. The method of claim 1, wherein the receptor comprises a compound of the general formula:

$(R^1)_n$—X—$(R^2)_m$ wherein X is a benzene ring, n is 3, in is 3; and wherein each of $R^1$ independently represents —$CH_2$—$NH_2$; and wherein each of $R^2$ independently represents hydrogen, alkyl, alkenyl, or alkynyl.

11. The method of claim 10 wherein the indicator comprises 5-carboxyfluoroscein.

12. A method for determining a concentration of citric acid in a solution, the method comprising:

adding the solution comprising the citric acid to a composition, the composition comprising a receptor for the citric acid, an indicator, and a solvent, the receptor being adapted to bind to the citric acid during use, the indicator beings adapted to bind to the receptor such that at least one physical property of the indicator are altered during use, wherein the receptor comprises a compound of the formula:

$(R^1)_n$—X—$(R^2)_m$ wherein X comprises carbocyclic systems or $C_1$–$C_{10}$ alkanes, n is an integer of at least 3, m is an integer of at least 1; and wherein each of $R^1$ independently represents —$(CH2)_y$—$NR^3$—$C(NR^4)$—$NR^5$, or —$(CH_2)_y$—$NR^6R^7$;

where y is an integer of at least 1;

where $R^3$, $R^4$, and $R^5$ independently represent hydrogen, alkyl, aryl, alkyl carbonyl of 1 to 10 carbon atoms, or alkoxy carbonyl of 1 to 10 carbon atoms, or $R^4$ and $R^5$ together represent a cycloalkyl group;

where $R^6$ represents hydrogen, alkyl, aryl, alkyl carbonyl of 1 to 10 carbon atoms, or alkoxy carbonyl of 1 to 10 carbon atoms; where $R^7$ represents hydrogen, alkyl, aryl, alkyl carbonyl of 1 to 10 carbon atoms, or alkoxy carbonyl of 1 to 10 carbon atoms; or where $R^6$ and $R^7$ together represent a cycloalkyl group; and wherein each of $R^2$ independently represents hydrogen, alkyl, alkenyl, alkynyl, phenyl, phenylalkyl, arylalkyl aryl, or together with another group represent a carbocyclic ring;

allowing the polycarboxylic acid to interact with the receptor to substantially release the indicator from the receptor;

moitoring the change in the physical property of the indicator after the addition of the solution; and calculating the concentration of the citric acid in the solution based on the change in physical property of the indicator.

13. The method of claim 12, wherein monitoring the chance in the physical property of the indicator comprises measuring the absorption of the composition, and wherein monitoring the change in the physical property of the indicator comprises measuring the fluorescence of the composition.

14. The method of claim 12, further comprising adjusting the pH of the solution of the citric acid to a value of at least 5.0 prior to adding the solution to the composition, and wherein the solution of the citric acid is filtered prior to adding the solution to the composition.

15. The method of claim 12, wherein monitoring the change in the physical property of the indicator comprises measuring the change in absorption of the composition.

16. The method of claim 12, wherein monitoring the change in the physical property of the indicator comprises measuring the fluorescence of the composition.

17. The method of claim 12, wherein the solution of the citric acid is filtered prior to adding the solution to the composition.

18. The method of claim 12, further comprising adjusting the pH of the solution of the polycarboxylic acid to a value of at least 5.0 prior to adding the solution to the composition.

19. The method of claim 12, wherein a binding strength of the receptor to the indicator is less than a binding strength of the receptor to the citric acid.

20. The method of claim 12 wherein the receptor comprises a compound of the general formula:

$(R^1)_n$—X—$(R^2)_m$ wherein X is a benzene ring, n is an integer of at least 3, m is an integer of 1 to 3;

wherein each of $R^1$ independently represents —$(CH_2)_y$—$NR^3$—$C(NR^4)$—$NR^5$;

where y is an integer of 1 to 10;

where $R^3$, $R^4$, and $R^5$ independently represents hydrogen, alkyl, aryl, alkyl carbonyl of 1 to 10 carbon atoms, or alkoxy carbonyl of 1 to 10 carbon atoms, or $R^4$ and $R^5$ together represent a cycloalkyl group; and wherein each of $R^2$ independently represents hydrogen, alkyl, alkenyl, or alkynyl.

21. The method of claim 12 wherein the receptor comprises a compound of the general formula:

$(R^1)_n$—X—$(R^2)_m$ wherein X is a benzene ring, n is 3, m is 3; and wherein each of $R^1$ independently represents —$CH_2$—$NH_2$; and wherein each of $R^2$ independently represents hydrogen, alkyl, alkenyl, or alkynyl.

22. The method of claim 21 wherein the indicator comprises 5-carboxyfluoroscein.

* * * * *

UNITED STATES PATENT AND TRADEMARK OFFICE
CERTIFICATE OF CORRECTION

PATENT NO. : 6,048,732  
DATED : April 11, 2000  
INVENTOR(S) : Eric V. Anslyn and Axel Metzger Page 1 of 1

It is certified that error appears in the above-identified patent and that said Letters Patent is hereby corrected as shown below:

<u>Column 12, claim 1,</u>  
Line 7, please change "are" to -- is --  
Line 15, please change "-CH2)$_y$-" to -- -(CH$_2$)$_y$- --  
Line 30, please change "phelnyl" to -- phenyl --  
Line 37, please change "receptors" to -- receptor --

<u>Column 13, claim 10,</u>  
Line 4, please change "in" to -- m --

<u>Column 13, claim 12,</u>  
Line 37, please change "beings" to -- being --  
Line 38, please change "are" to -- is --  
Line 46, please change "-CH2)$_y$-" to -- -(CH$_2$)$_y$- --

Signed and Sealed this

Second Day of April, 2002

*Attest:*

*Attesting Officer*

JAMES E. ROGAN  
*Director of the United States Patent and Trademark Office*